United States Patent
Imura et al.

(10) Patent No.: US 10,344,250 B2
(45) Date of Patent: Jul. 9, 2019

(54) AZEOTROPIC COMPOSITION HAVING FLUORINE-CONTAINING OLEFIN AS CONSTITUENT

(71) Applicant: Central Glass Company, Limited, Ube-shi, Yamaguchi (JP)

(72) Inventors: Hideaki Imura, Fujimino (JP); Naoto Takada, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 63 days.

(21) Appl. No.: 15/528,318

(22) PCT Filed: Oct. 20, 2015

(86) PCT No.: PCT/JP2015/079494
§ 371 (c)(1),
(2) Date: May 19, 2017

(87) PCT Pub. No.: WO2016/080133
PCT Pub. Date: May 26, 2016

(65) Prior Publication Data
US 2017/0321167 A1 Nov. 9, 2017

(30) Foreign Application Priority Data
Nov. 21, 2014 (JP) .................................. 2014-237179

(51) Int. Cl.
*C11D 1/00* (2006.01)
*C11D 7/50* (2006.01)
(Continued)

(52) U.S. Cl.
CPC ............ *C11D 7/504* (2013.01); *C07C 21/073* (2013.01); *C07C 21/18* (2013.01); *C11D 7/30* (2013.01);
(Continued)

(58) Field of Classification Search
None
See application file for complete search history.

(56) References Cited

U.S. PATENT DOCUMENTS 5,250,208 A * 10/1993 Merchant ................. C08J 9/149
134/12
6,759,381 B1 7/2004 Johnson et al.
(Continued)

FOREIGN PATENT DOCUMENTS

CN 1076951 A 10/1993
CN 1487986 A 4/2004
(Continued)

OTHER PUBLICATIONS

International Search Report (PCT/ISA/210) issued in PCT Application No. PCT/JP2015/079494 dated Jan. 19, 2016 with English translation (five pages).
(Continued)

*Primary Examiner* — Necholus Ogden, Jr.
(74) *Attorney, Agent, or Firm* — Crowell & Moring LLP

(57) ABSTRACT

A liquid composition according to one embodiment of the present invention contains 0.0001 mol % to 40 mol % (Z)-1,2-dichloro-3,3,3-trifluoropropene (1223Z) and 99.9999 mol % to 60 mol % (E)-1,2-dichloro-ethylene (t-DCE). The liquid composition has less influence on the global environment and azeotropic (or azeotrope-like) properties. There occurs practically no composition change even when the liquid composition is used in an open system or used for a long term. Further, it is less likely that there will occur a composition change even when the liquid composition is recovered by distillation. The liquid composition is thus suitably usable as a cleaning agent (solvent). In particular, the liquid composition of 90 mol % or less of t-DCE is classified as non-hazardous under the Fire Serves Act.

12 Claims, 1 Drawing Sheet

(51) Int. Cl.
  *C11D 7/30* (2006.01)
  *C07C 21/18* (2006.01)
  *C07C 21/073* (2006.01)

(52) U.S. Cl.
  CPC .............. *C11D 7/50* (2013.01); *C11D 7/5018* (2013.01); *C11D 7/5059* (2013.01)

(56) References Cited

U.S. PATENT DOCUMENTS

| | | |
|---|---|---|
| 2002/0137645 A1 | 9/2002 | Pham et al. |
| 2010/0004155 A1 | 1/2010 | Ishihara et al. |
| 2011/0041529 A1 | 2/2011 | Chen et al. |
| 2011/0309287 A1 | 12/2011 | Chen et al. |
| 2012/0304686 A1 | 12/2012 | Kontomaris |
| 2015/0191405 A1 | 7/2015 | Nishiguchi et al. |
| 2015/0191406 A1 | 7/2015 | Nishiguchi et al. |
| 2015/0353800 A1 | 12/2015 | Kujak |

FOREIGN PATENT DOCUMENTS

| | | |
|---|---|---|
| CN | 1816507 A | 8/2006 |
| CN | 102015595 A | 4/2011 |
| CN | 102292469 A | 12/2011 |
| JP | 2-221388 A | 9/1990 |
| JP | 2-221389 A | 9/1990 |
| JP | 2-221962 A | 9/1990 |
| JP | 2-222469 A | 9/1990 |
| JP | 2-222496 A | 9/1990 |
| JP | 2-222702 A | 9/1990 |
| JP | 2004-529087 A | 9/2004 |
| JP | 2006-525374 A | 11/2006 |
| JP | 2008-133438 A | 6/2008 |
| WO | WO 2014/046250 A1 | 3/2014 |
| WO | WO 2014/046251 A1 | 3/2014 |
| WO | WO 2014/117014 A2 | 7/2014 |
| WO | WO 2014/144558 A1 | 9/2014 |

OTHER PUBLICATIONS

Japanese-language Written Opinion (PCT/ISA/237) issued in PCT Application No. PCT/JP2015/079494 dated Jan. 19, 2016 (three pages).

Chinese-language Office Action issued in counterpart Chinese Application No. 201580062994.2 dated Nov. 16, 2018 (six (6) pages).

* cited by examiner

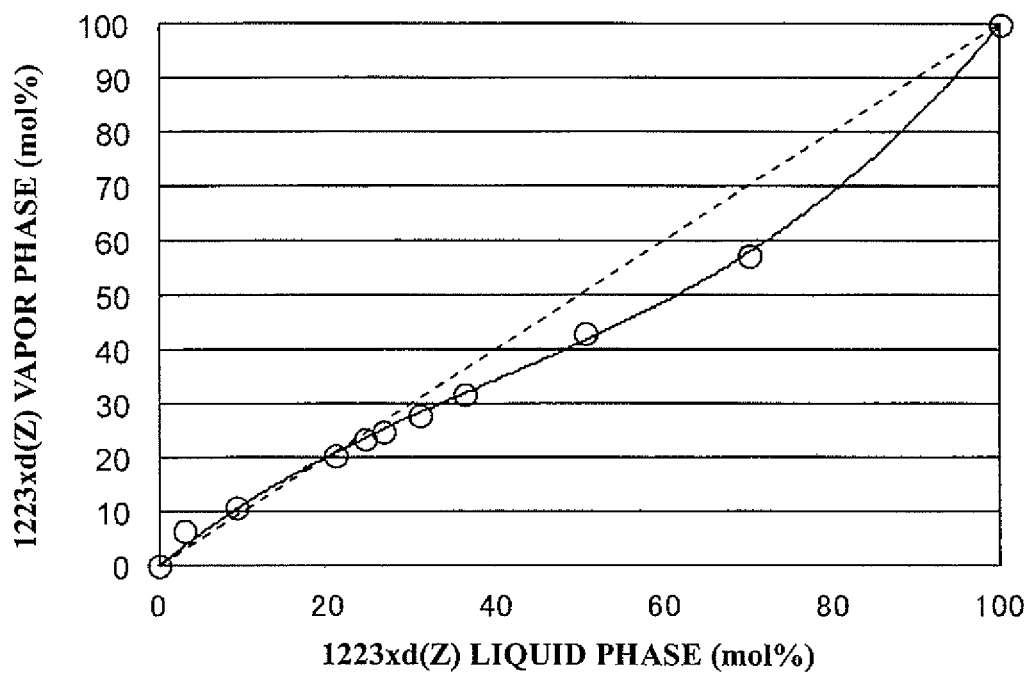

ated as
AZEOTROPIC COMPOSITION HAVING FLUORINE-CONTAINING OLEFIN AS CONSTITUENT

FIELD OF THE INVENTION

The present invention relates to a novel composition containing a fluorine-containing olefin.

BACKGROUND ART

It is known that fluorine-containing alkanes of 1 to 5 carbon atoms, such as chlorofluorocarbons (abbreviated as "CFCs"), hydrochlorofluorocarbons (abbreviated as "HCFCs") and hydrofluorocarbons (abbreviated as "HFCs"), show volatility, stability and non-flammability. These fluorine-containing alkanes (also sometimes referred to as "Freons") have thus been used as refrigerants, working fluids, foaming agents, sprays, cleaning agents, dissolving agents, solvents, etc. and made contributions to industrial developments. Further, these fluorine-containing alkanes have been widely used as blends of two or more kinds thereof. For example, there were commonly used mixed refrigerants R502, R507A, R404A, R407C and R401A according to the American Society of Heating, Refrigerating and Air-Conditioning Engineers (ASHRAE) standards. The above mixed refrigerants are each prepared by mixing two or more kinds of Freons at a specific ratio for improvements in coefficient of performance, refrigeration cycle, non-flammability, global warming potential and the like. Because of the volatility of the fluorine-containing alkanes, however, there occurs a composition change in the mixture by evaporation of any one of the Freons during use. The physical properties of the mixture vary due to such a composition change. It is thus preferable to form an azeotropic or azeotrope-like composition in that the vapor phase produced by volatilization has the same or substantially the same composition as does the liquid phase. The above-mentioned refrigerant R502 (that is, a mixed refrigerant of R22 and R115) and refrigerant R507A (that is, a mixed refrigerant of R143a and R125) are known as azeotropic refrigerants because each of these refrigerants is in the form of an azeotropic mixture having vapor and liquid phases of exactly the same composition. The above-mentioned refrigerant R410A is known as an azeotrope-like refrigerant because its constituent components R32 and R125 do not form an azeotropic mixture but form a mixture having vapor and liquid phases of substantially the same composition so that this mixture can be handled in practically the same manner as the azeotropic mixture. The applications other than the refrigerant applications include water removing agents each prepared by blending a fluorine-containing alkane with an alcohol, and cleaning agents each prepared by adding a non-flammable fluorine-containing alkane to a flammable hydrocarbon solvent so as to achieve non-flammability and controlled cleaning power. Even in these water removing/cleaning agent applications, as in the case of the refrigerant applications, it is preferable to form an azeotropic or azeotrope-like composition in that the vapor phase produced by volatilization has the same or substantially the same composition as does the liquid phase.

It is also known that the fluorine-containing alkanes as mentioned above are very stable in the air and long in atmospheric lifetime and become a cause of global warming. For these reasons, fluorine-containing olefins of 2 to 5 carbon atoms (such as hydrofluoroolefins, hydrochlorofluoroolefins, chlorofluoroolefins and fluoroolefins) have recently been proposed as substitutes for the above fluorine-containing alkanes. The fluorine-containing olefins, each of which has a double bond in the molecule, shows significantly high reactivity to OH radicals in the air as compared to the fluorine-containing alkanes with no double bond. The atmospheric lifetime of the fluorine-containing olefins is generally in days, whereas the atmospheric lifetime of the commonly used fluorine-containing alkanes such as HFC-365mfc, HFC-245fa and HFC-43-10 is in years. The fluorine-containing olefins, even if released into the air, get quickly decomposed and have less influence of global warming, ozone depletion etc. Further, it is reported that the fluorine-containing olefins have similar physical properties as those of the fluorine-containing alkanes and can be used for various applications such as refrigerants, working fluids, foaming agents, sprays, cleaning agents, dissolving agents, solvents, etc. The fluorine-containing olefins can be improved in performance by blending as in the case of the fluorine-containing alkanes. For example, Patent Document 1 teaches that: an azeotrope-like binary solvent system is formed by mixing of (Z)-1-chloro-3,3,3-trifluoropropene with 1,1,2,2-tetrafluoro-1-methoxyethane; and the thus-formed binary solvent has good cleaning effect on various oils. However, specific reports on azeotropic or azeotrope-like mixtures of fluorine-containing olefins are few in number as compared to those of fluorine-containing alkanes.

Patent Document 2 teaches a mixture of a fluorine-containing olefin of 3 carbon atoms and a general-purpose solvent and, in particular, discloses a degreasing test of 1,2-dichloro-3,3,3-trifluoropropene alone as Example 4. Patent Document 2 however gives no specific description about a mixture of 1,2-dichloro-3,3,3-trifluoropropene and flammable (E)-1,2-dichloro-ethylene (flash point: 2 to 4° C.) and its cleaning power, evaporation behavior, flammability or the like. Although 1,2-dichloro-3,3,3-trifluoropropene exists as geometric E- and Z-isomers that have intrinsic boiling points and polarities and thereby differ in drying property, cleaning power and polymer compatibility, Patent Document 2 gives no description about these geometric isomers. Patent Documents 3 to 7 teaches a resist remover, a buffing agent, an adhesive moisture removing solvent and a dry cleaning agent, but give no description about the geometric isomers of 1,2-dichloro-3,3,3-trifluoropropene and the detailed behavior of a blend of 1,2-dichloro-3,3,3-trifluoropropene and (E)-1,2-dichloro-ethylene as in the case of Patent Document 2.

PRIOR ART DOCUMENTS

Patent Documents

Patent Document 1: Japanese Laid-Open Patent Publication No. 2008-133438
Patent Document 2: Japanese Laid-Open Patent Publication No. H12-221388
Patent Document 3: Japanese Laid-Open Patent Publication No. H2-221962
Patent Document 4: Japanese Laid-Open Patent Publication No. H2-221389
Patent Document 5: Japanese Laid-Open Patent Publication No. H2-222469
Patent Document 6: Japanese Laid-Open Patent Publication No. H2-222496
Patent Document 7: Japanese Laid-Open Patent Publication No. H2-222702

SUMMARY OF THE INVENTION

Problems to be Solved by the Invention

As discussed above, the volatile solvent composition can be improved in performance by simply mixing a plurality of solvents, but cannot avoid the problem that a liquid composition change is likely to occur due to the volatility of the respective components. When the binary liquid composition is used for cleaning in an ultrasonic cleaning machine, for example, the low boiling component (i.e. high vapor pressure component) is generally preferentially volatilized so that the high boiling component (i.e. low vapor pressure component) is concentrated in a cleaning tank. In the case of using the low boiling component of high cleaning power and the high boiling component of low cleaning power, there may arises the problem of insufficient cleaning as the amount of the low boiling component in the liquid composition decreases with time. The used cleaning liquid is generally recovered and regenerated by distillation operation. It is however necessary to adjust the liquid composition of the recovered cleaning liquid, which is not efficient in operation, in the case where the liquid phase is different in composition from the vapor phase.

In particular, there is a demand to provide a non-flammable composition of (E)-1,2-dichloro-ethylene in view of the fact that the flash point of (E)-1,2-dichloro-ethylene is 2 to 4° C. Since the non-flammable composition may vary in cleaning power and change to a flammable composition due to a liquid composition change by volatilization during use, it is strongly demanded to form an azeotropic or azeotrope-like composition in that the vapor phase produced by volatilization has the same or substantially the same composition as does the liquid phase.

It is accordingly an object of the present invention to provide a novel azeotropic or azeotrope-like composition that contains environment-friendly (Z)-1,2-dichloro-3,3,3-trifluoropropene and causes no composition change by volatilization.

Means for Solving the Problems

The present inventors have made extensive researches to solve the above problems. As a result of the extensive researches, it has been found that: a Z-isomer of 1,2-dichloro-3,3,3-trifluoropropene (also sometimes referred to as "HCFO-1223xd(Z)" or "1223Z") and (E)-1,2-dichloro-ethylene (also sometimes referred to as "t-DCE") form an azeotropic (or azeotrope-like) composition; the composition of 0.0001 mol % to 40 mol % of 1223Z and 99.9999 mol % to 60 mol % oft-DEC is azeotrope-like in that the vapor and liquid phases are substantially the same in composition; and the composition of 90 mol % or less of t-DCE is non-flammable with no-flash point under the Fire Serves Act. It has also been found that the composition of 20 mol % of 1223Z and 80 mol % of t-DCE corresponds to an azeotropic point. Further, it has been confirmed by the after-mentioned working examples that the azeotropic composition according to the present invention is useful as a degreasing agent. The present invention is based on these findings.

Namely, the present invention involves the following inventive aspects.

[Inventive Aspect 1]
An azeotropic (or azeotrope-like) composition comprising (Z)-1,2-dichloro-3,3,3-trifluoropropene (1223Z) and (E)-1,2-dichloro-ethylene (t-DCE).

[Inventive Aspect 2]
The azeotropic (or azeotrope-like) composition according to Inventive Aspect 1, wherein the azeotropic (or azeotrope-like) composition contains 0.0001 mol % to 40 mol % of 1223Z and 99.9999 mol % to 60 mol % oft-DCE.

[Inventive Aspect 3]
The azeotropic (or azeotrope-like) composition according to Inventive Aspect 1 or 2, wherein the azeotropic (or azeotrope-like) composition is non-flammable and contains 10 mol % to 40 mol % of 1223Z and 90 mol % to 60 mol % oft-DCE.

[Inventive Aspect 4]
An azeotropic composition consisting of 20 mol % of (Z)-1,2-dichloro-3,3,3-trifluoropropene (1223Z) and 80 mol % of (E)-1,2-dichloro-ethylene (t-DCE).

[Inventive Aspect 5]
A liquid composition comprising the azeotropic (or azeotrope-like) composition according to any one of Inventive Aspects 1 to 4 and at least one additional component.

[Inventive Aspect 6]
A liquid composition comprising the azeotropic (or azeotrope-like) composition according to any one of Inventive Aspects 1 to 4 and 10 ppm to 30 mass % of at least one additional component relative to a total amount of the azeotropic (or azeotrope-like) composition.

[Inventive Aspect 7]
A solvent for cleaning, comprising the azeotropic (or azeotrope-like) composition or liquid composition according to any one of Inventive Aspects 1 to 6.

[Inventive Aspect 8]
A method for cleaning a cleaning target object, comprising bringing the azeotropic (or azeotrope-like) composition or liquid composition according to any one of Inventive Aspects 1 to 6 into contact with the cleaning target object.

In the present invention, it is possible to provide the novel azeotropic (or azeotrope-like) liquid composition. This liquid composition has the effect of maintaining its performance as a liquid that is less likely to cause a composition change even when used in an open system. Further, this azeotropic (or azeotrope-like) liquid composition poses less load on the environment. In particular, the composition of 10 mol % to 40 mol % of 1223Z and 90 mol % to 60 mol % oft-DCE is classified as non-hazardous under the Fire Serves Act. The azeotropic (or azeotrope-like) composition according to the present invention is useful as a solvent (or cleaning agent) for cleaning away a contaminant such as foreign matter, oil and fat etc.

BRIEF DESCRIPTION OF THE DRAWINGS

FIG. 1 is a vapor-liquid equilibrium diagram of (Z)-1,2-dichloro-3,3,3-trifluoropropene (1223Z) and (E)-1,2-dichloro-ethylene (t-DCE).

DETAILED DESCRIPTION OF THE EMBODIMENTS

Hereinafter, the present invention will be described in detail below.

It is feasible to easily form a uniform composition of a fluorine-containing olefin due to the fact that fluorine-containing olefin shows high compatibility with various solvents. Such a simple composition however has the problem it is likely to cause a "liquid composition change". Namely, the composition, when prepared by mixing a plurality of liquids while ensuring compatibility, cannot avoid the problem that a liquid composition change is likely to occur due to the volatility of the respective components.

When the binary liquid composition is used as a cleaning agent in an ultrasonic cleaning machine, for example, the high volatile, low boiling component (i.e. high vapor pressure component) is generally preferentially volatilized so that the low volatile, high boiling component (i.e. low vapor pressure component) is concentrated in a cleaning tank. In the case of using the low boiling component of high cleaning power and the high boiling component of low cleaning power, there may arises the problem of insufficient cleaning as the amount of the low boiling component in the cleaning agent decreases with time. In the case of preparing the cleaning agent as a non-flammable composition by blending the non-flammable solvent with the flammable solvent, the cleaning agent may change to a flammable composition by preferential volatilization of the non-flammable component.

In terms of environmental protection and cost efficiency, it is desirable to recover and recycle the used cleaning agent by e.g. distillation operation. In the case of the binary liquid system, however, the two liquid components of different boiling points generally need to be separately recovered. Thus, this recovery and recycling operation tends to cause an operational burden.

The same problem arises when the liquid composition is used as a working fluid in a thermodynamic cycle. Namely, there is a possibility of a liquid composition change during long-term use when the liquid composition is used as the working fluid in the thermodynamic cycle. The heat capacity, viscosity or lubricating oil affinity of the liquid composition varies due to such a liquid composition change. This can lead to a deterioration in the working performance of the thermodynamic cycle.

The binary (multicomponent) liquid composition, when used as the cleaning agent or the working fluid, has to be frequently analyzed and constantly maintained within a proper composition range by mixing the components at an appropriate ratio and adding the volatilized component. This liquid composition management becomes a large operational burden.

By contrast, an azeotropic composition is particularly preferred in that the vapor phase caused by vaporization has the same composition as does the liquid phase whereby there is unlikely to occur a liquid composition change during use.

In the present specification, the term "azeotropic" is used in the thermodynamically exact sense. For example, a liquid mixture of ethanol (96 mass %) and water (4 mass %) is an azeotropic mixture (azeotrope) in that the vapor in equilibrium with the liquid also has a composition of ethanol (96 mass %) and water (4 mass %), i.e. the vapor and liquid phases are exactly the same in composition. The term "azeotropic" is used to refer to such a phenomenon. Under a specific temperature and pressure, the azeotrope exists only at one composition point.

The term "azeotrope-like" is also called as "quasi-azeotropic". There is a case where a liquid mixture of certain composition range may show a phenomenon in which the vapor and liquid phases in equilibrium are substantially the same in composition even though it is not azeotropic in the thermodynamically exact sense. This mixture can be handled in the same manner as the azeotropic mixture as long as the vapor and liquid phases in equilibrium are substantially the same in composition but not exactly the same in composition. In that, it is preferable that the difference between the compositions of the vapor and liquid phases in equilibrium is as small as possible. The term "azeotrope-like" or "quasi-azeotropic" is used to refer to the phenomenon in which the vapor and liquid phases in equilibrium are substantially the same in composition. The composition showing such a phenomenon is referred to as "azeotrope-like or quasi-azeotropic composition".

In academic fields, the terms "azeotropic" and "azeotrope-like (or quasi-azeotropic)" should be distinguished. In practical applications such as cleaning, however, there is no need to distinguish the terms "azeotropic" and "azeotrope-like (or quasi-azeotropic)" because the azeotropic composition and the azeotrope-like (or quasi-azeotropic) composition can be handled in the same manner. For this reason, the terms "azeotropic" and "azeotrope-like (or quasi-azeotropic)" are collectively referred to as "azeotropic (or azeotrope-like)" in the present specification. The azeotropic or azeotrope-like composition is referred to as "azeotropic (or azeotrope-like) composition". It does not matter whether or not the azeotropic (or azeotrope-like) composition has an azeotropic point. The azeotropic (or azeotrope-like) composition can be any composition in which the vapor and liquid phases in equilibrium are substantially the same in composition.

The azeotrope-like composition is not derived based on theory, but is found out for the first time at the time when, during experimental researches on various kinds and composition ratios of liquids, the compositions of the vapor and liquid phases becomes substantially identical. The present invention has been established by conducting vapor-liquid equilibrium experiment of the Z-isomer of 1,2-dichloro-3,3,3-trifluoropropene and (E)-1,2-dichloro-ethylene and finding out the azeotropic point at which the vapor and liquid phases are exactly the same in composition as well as the azeotrope-like composition in which the vapor and liquid phases are substantially the same in composition.

There exist E and Z isomers of 1,2-dichloro-3,3,3-trifluoropropene. A method for selective synthesis of the Z isomer of 1,2-dichloro-3,3,3-trifluoropropene is disclosed in various patent documents (e.g. International Publication No. WO 2014/046250 and No. WO 2014/046251). It is feasible to obtain the high-purity Z isomer (1223E) by precision distillation. On the other hand, (E)-1,2-dichloro-ethylene is commercially available as a flammable solvent (flash point: 2 to 4° C.).

As is clear from a vapor-liquid equilibrium diagram shown in the after-mentioned working example, the composition containing 0.0001 mol % to 40 mol % of 1223E as the first component and 99.9999 mol % to 60 mol % of t-DCE as the second component is azeotropic (or azeotrope-like) in that the vapor and liquid phases are substantially the same in composition. Herein, the unit "mol %" refers to % by mole number of each component (i.e. relative mol % fractions of two components) assuming that the sum of the mole number of 1223Z and the mole number of t-DCE is 100. In the above specific composition range, it is less likely that there will occur a composition change even when the liquid composition is practically handled in an open system or when the liquid composition is subjected to recovery by distillation operation.

When the molar ratio of 1223Z/t-DCE is in the range of 0.0001/99.9999 to 25/75, the vapor and liquid phases are closer in composition so that a composition change is further less likely to occur. It is preferable in the present invention that the molar ratio of 1223Z/t-DCE is in the range of 10/90 to 25/75 because, in such a composition range, the composition is not only less likely to cause a liquid composition change and but also classified as non-flammable under the Fire Serves Act.

It is particularly preferable in the present invention that the azeotropic (or azeotrope-like) composition contains 19 to 21 mol % of 1223E as the first component and 81 to 78 mol % of t-DCE as the second component because, in such a composition range, the composition is not only non-flammable but also very less likely to cause a liquid composition change. The composition containing 20 mol % of 1223E as the first component and 80 mol % of t-DCE as the second component is an azeotrope that does not theoretically cause a composition change.

The azeotropic (or azeotrope-like) composition according to the present invention is prepared by mixing the above-specific amounts of the first and second components. Needless to say, it is one preferred embodiment of the present invention that the azeotropic (or azeotrope-like) composition has high purity with substantially no impurity. Depending on the purpose of use, however, the liquid composition is not necessarily so high in purity. In such a case, it is feasible to use the first component 1223E and the second component t-DCE in which raw materials used for the synthesis of the respective components or by-products thereof remain in small amounts (each component remains in an amount of generally less than 1 wt % relative to the total amount of the azeotropic (or azeotrope-like) composition.

In the case where the azeotropic (or azeotrope-like composition) needs to have high purity, on the other hand, it is preferable to prepare the azeotropic (or azeotrope-like) composition by mixing the first component 1223E and the second component t-DCE after removing raw material-derived impurities from these two components by precision distillation and thereby increasing the purity of the respective components.

For the purpose of improving the performance of the azeotropic (or azeotrope-like) composition, an additional component may preferably be added to the azeotropic (or azeotrope-like) composition as needed. As the additional component, there can be used a cleaning power improving agent (e.g. surfactant), a stabilizer (e.g. acid acceptor, antioxidant) and the like. Specific examples of such an additional component are nonionic surfactants as typified by: sorbitan fatty acid esters such as sorbitan monooleate and sorbitan trioleate; polyoxyethylene sorbitol fatty acid esters such as sorbitol tetraoleate of polyoxylethylene; polyoxyethylene glycol fatty acid esters such as polyoxyethylenemonolaurate; polyoxyethylene alkyl ethers such as polyoxyethylene lauryl ether; polyoxyethylene alkyl phenyl ethers such as polyoxyethylene nonyl phenyl ether, and polyoxyethylene alkylamine fatty acid amides such as polyoxylethylene oleic amide. These surfactants can be used solely or in combination of two or more kinds thereof. In the case where the azeotropic or azeotrope-like composition is used in a cleaning agent, a cationic surfactant or anionic surfactant may be added in addition to the nonionic surfactant for the purpose of synergistic improvements in cleaning power and interfacial action. The amount of the surfactant added to the azeotropic or azeotrope-like composition varies depending the kind of the surfactant used, and can be adjusted within the range that does not impair the azeotropic or azeotrope-like properties of the azeotropic or azeotrope-like composition. In general, the amount of the surfactant added to the azeotropic or azeotrope-like composition is in the range of 0.1 mass % to 30 mass %, preferably 0.3 mass % to 5 mass %.

Various stabilizers may be added for uses under severe conditions. Although there is no particular limitation on the kind of the stabilizer used, the stabilizer used is preferably of the kind capable of being entrained and distilled by distillation operation or capable of forming an azeotrope-like mixture. As such a stabilizer, there can be used a nitro compound, an epoxy compound, a phenol, an imidazole, an amine, a hydrocarbon and the like.

The nitro compound can be a known compound or an aliphatic and/or aromatic derivative thereof. Specific examples of the nitro compound are: aliphatic nitro compounds such as nitromethane, nitroethane, 1-nitropropane and 2-nitropropane; and aromatic nitro compounds such as nitrobenzene, o-, m- or p-dinitrobenzene, trinitrobenzene, o-, m- or p-nitrotoluene, o-, m- or p-ethylnitrobenzene, 2,3-, 2,4-, 2,5-, 2,6-, 3,4- or 3,5-dimethylnitrobenzene, o-, m- or p-nitroacetophenone, o-, m- or p-nitrophenol and o-, m- or p-nitroanisol.

Specific examples of the epoxy compound are: monoepoxy compounds such as ethylene oxide, 1,2-butylene oxide, propylene oxide, styrene oxide, cyclohexene oxide, glycidol, epichlorohydrin, glycidyl methacrylate, phenyl glycidyl ether, allyl glycidyl ether, methyl glycidyl ether, butyl glycidyl ether and 2-ethylhexyl glycidyl ether; and polyepoxy compounds such as diepoxybutane, vinylcyclohexene dioxide, neopentyl glycol diglycidyl ether, ethylene glycol diglycidyl ether, glycerine polyglycidyl ether and trimethylolpropane triglycidyl ether.

Specific examples of the phenol are those having not only a hydroxy group but also any of various substituents e.g. alkyl group, alkenyl group, alkoxy group, carboxyl group, carbonyl group and halogen atom, as typified by: monovalent phenols such as 2,6-di-t-butyl-p-cresol, o-cresol, m-cresol, p-cresol, thymol, p-t-butylphenol, o-methoxyphenol, m-methoxyphenol, p-methoxyphenol, eugenol, isoeugenol, butylhydroxyanisole, phenol and xylenol; and divalent phenols such as t-butylcatechol, 2,5-di-t-aminohydroquinone and 2,5-di-t-butylhydroquinone.

Specific examples of the imidazole are those having a straight or branched alkyl, cycloalkyl or aryl group of 1 to 18 carbon atoms as a N-position substituent, as typified by 1-methylimidazole, 1-n-butylimidazole, 1-phenylimidazole, 1-benzylimidazole, 1-(β-oxyethyl)imidazole, 1-methyl-2-propylimidazole, 1-methyl-2-isobutylimidazole, 1-n-butyl-2-methylimidazole, 1,2-dimethylimidazole, 1,4-dimethylimidazole, 1,5-dimethylimidazole, 1,2,5-trimethylimidazole, 1,4,5-trimethylimidazole and 1-ethyl-2-methylimidazole. These compounds can be used solely or in combination of two or more kinds thereof.

Specific examples of the amine are pentylamine, hexylamine, diisopropylamine, diisobutylamine, di-n-propylamine, diallylamine, triethylamine, N-methylaniline, pyridine, morpholine, N-methylmorpholine, triallylamine, allylamine, α-methylbenzylamine, methylamine, dimethylamine, trimethylamine, ethylamine, diethylamine, propylamine, isopropylamine, dipropylamine, butylamine, isobutylamine, dibutylamine, tributylamine, dipentylamine, tripentylamine, 2-ethylhexylamine, aniline, N,N-dimethylaniline, N,N-diethylaniline, ethylenediamine, propylenediamine, diethylenetriamine, tetraethylenepentamine, benzylamine, dibenzylamine, diphenylamine and diethylhydroxylamine. These amines can be used solely or in combination of two or more kinds thereof.

Specific examples of the hydrocarbon are α-methylstyrene, p-isopropenyltoluene, isoprenes, propadienes and terpenes. These hydrocarbons can be used solely or in combination of two or more kinds thereof.

<Use as Cleaning Agent or Solvent>

The azeotropic (or azeotrope-like) composition (or the liquid composition containing the azeotropic (or azeotrope-like) composition) according to the present invention is suitable for cleaning away a foreign matter, oil or fat, grease, wax, flux, ink etc. from precision machinery parts, electronic materials (such as printed boards, liquid crystal displays, magnetic recording parts and semiconductor materials), resin processing parts, optical lens, clothing products and the like. As mentioned above, the azeotropic (or azeotrope-like) composition according to the present invention shows non-flammability as well as adequate flowability and solubility and thus can be used to remove the foreign matter (e.g. particulate matter) by washing away or dissolution. There is no particular limitation on the cleaning technique. The precision machinery part or electronic material can be cleaned with the azeotropic (or azeotrope-like) composition by immersion washing, wiping using a waste cloth, spray cleaning treatment or the like. These techniques may be used in combination. It is one preferred embodiment of the present invention to put the azeotropic (or azeotrope-like) composition as a cleaning liquid in an ultrasonic cleaning machine, immersing the cleaning target object in the cleaning liquid and perform ultrasonic cleaning treatment of the cleaning target object with the cleaning liquid.

Furthermore, the azeotropic (or azeotrope-like) composition according to the present invention causes almost no composition change even when used in an open system as mentioned above. There is thus obtained a great merit in practical use that it is possible to ensure stable cleaning power with not-so-frequent composition management.

It is feasible to recover the azeotropic (or azeotrope-like composition) according to the present invention by subjecting the used cleaning liquid to recovery and distillation operation and thereby removing the foreign matter, oil or fat etc. from the liquid composition. Since ordinary distillation regeneration apparatuses for cleaning agents adopt a simple distillation system, the azeotropic or azeotrope-like composition containing 0.0001 mol % to 40 mol % of 1223Z as the first component and 99.9999 mol % to 60 mol % of t-DCE as the second embodiment according to the present invention can be regenerated by a commercially available distillation regeneration apparatus with causing substantially no composition change. The azeotropic composition is preferred in that there occurs no composition change even when the azeotropic composition is subjected to distillation operation by a distillation column with a large plate number.

During the distillation operation, the respective two kinds of liquid components, 1223Z and t-DCE, maintain the properties of the azeotropic (or azeotrope-like) composition. The thus-recovered liquid composition is thus reusable as the cleaning solvent. In the case where the additional component is used as mentioned above, there is a possibility that the additional component may be removed by the distillation operation. In such a case, it is preferable to separately add the additional component.

EXAMPLES

The present invention will be described in more detail below by way of the following examples.

Example 1

In a 50-mL three-neck flask with a septum, a stirrer and a Dimroth condenser for refrigerant flow of −10° C., 1233Z and t-DCE were mixed in an amount of 25 mL in total at mole concentrations as shown in TABLE 1. A synthetic zeolite tube was attached to an upper side of the Dimroth condenser. The flask was immersed in an oil bath and, while stirring the mixture inside the flask, heated until the mixture was refluxed. The composition of the mixture was stabilized after 1 hour or more from the initiation of the reflux. After that, the thus-formed gas phase was sampled by a gastight syringe through the septum. This gas phase sample was analyzed by gas chromatography. Similarly, the thus-formed liquid phase was sampled in an amount of about 1 mL by a polypropylene syringe with a needle, and then, injected into a 2 mL vial cooled with ice water. This liquid phase sample was also analyzed by gas chromatography. The analysis results of the respective compositions are shown in TABLE 1 in terms of mol % with reference to a preset calibration curve. Further, the analysis results of TABLE 1 are plotted in FIG. 1 with the composition ratio of the 1223Z liquid phase as the horizontal axis and the composition ratio of the 1223Z vapor phase as the vertical axis. It is apparent from these results that the composition containing 40 to 99.9999 mol % of 1223Z as the first component and 0.0001 to 60 mol % of t-DCE as the second component is azeotropic or azeotrope-like with substantially no difference in composition between the vapor and liquid phases.

TABLE 1

| 1223Z Liquid Phase (mol %) | t-DCE Liquid Phase (mol %) | 1223Z Vapor Phase (mol %) | t-DCE Vapor Phase (mol %) |
| --- | --- | --- | --- |
| 100.0000 | 0.0000 | 100.0000 | 0.0000 |
| 70.1064 | 29.8936 | 57.3019 | 42.6981 |
| 50.7139 | 49.2861 | 43.0133 | 56.9867 |
| 36.3090 | 63.6910 | 31.8033 | 68.1967 |
| 31.0124 | 68.9876 | 27.8136 | 72.1864 |
| 26.7121 | 73.2879 | 24.7140 | 75.2860 |

TABLE 1-continued

| 1223Z Liquid Phase (mol %) | t-DCE Liquid Phase (mol %) | 1223Z Vapor Phase (mol %) | t-DCE Vapor Phase (mol %) |
|---|---|---|---|
| 24.5082 | 75.4918 | 23.4143 | 76.5857 |
| 21.0111 | 78.9889 | 20.3108 | 79.6892 |
| 9.2039 | 90.7961 | 10.7000 | 89.3000 |
| 3.0010 | 96.9990 | 6.4079 | 93.5903 |
| 0.0002 | 99.9998 | 0.0003 | 99.9997 |
| 0.0000 | 100.0000 | 0.0000 | 100.0000 |

Example 2

The flash point of mixed liquids of 1223Z and t-DCE were measured according to JIS K 2265-1 "Determination of Flash Point—Part 1: Tag Closed Cup Method". The measurement of the flash point was performed with the use of an automatic flash point tester atg-81 (manufactured by Tanaka Scientific Limited). The flash point measurement results of the respective liquid compositions are shown in TABLE 2. There was observed no flash point under atmospheric pressure condition within the azeotropic or azeotrope composition range of 1223Z and t-DCE.

TABLE 2

| 1223Z (mol %) | t-DCE (mol %) | Measurement Result |
|---|---|---|
| 30 | 70 | non-flammable |
| 20 | 80 | non-flammable |
| 10 | 90 | non-flammable |

Example 3

(Cleaning Test)

A commercially available 25-mL graduated cylinder was cut along the 11-mL graduation line. Further, a clean glass rod having a diameter of about 7.2 mm and a length of about 40 mm was provided. The mass of the glass rod was measured. The glass rod was immersed for 2 minutes in an oil shown in TABLE below, and then, drained by being held in a vertical position for 10 minutes (to remove excessive oil therefrom). The mass of the glass rod (more specifically, the total mass of the glass rod and the initial adhesive oil) was measured. After that, the glass rod was placed in the above-mentioned graduated cylinder. The azeotrope-like mixture of 20 mol % of 1223Z and 80 mol % of t-DCE as shown in TABLE 2 was poured into the graduated cylinder until the liquid level reached the 10-mL graduation line. The graduated cylinder was vertically positioned in the center of an ultrasonic cleaner (SW5800 manufactured by Citizen Systems Japan Co., Ltd.) filled with water. When ultrasonic waves were applied to the graduated cylinder in the ultrasonic cleaner, the azeotrope-like mixture was volatilized with time. At the time the liquid level reached the 8-mL graduation line, the composition inside the graduated cylinder was analyzed by gas chromatography. It was found that, in all experiments of Example 3, the liquid composition remained substantially the same before and after the cleaning test even though 2 mL of the mixture was volatilized. It has thus been shown that the azeotrope-like mixture used in Example 3 would maintain its azeotrope-like composition without causing substantially no composition change of the remaining liquid phase. Subsequently, the glass rod was dried. The mass of the glass rod (more specifically, the total mass of the glass rod and the remaining oil) was measured. The oil removing rate ({[mass of remaining oil]÷[mass of initial adhesive oil]}×100 [%]) was determined based on the measurement results. Further, the surface of the glass rod was observed with a microscope. In every experiment, the oil removing rate was 100%; and there was no oil residue found by microscopic observation so that the microscopic observation result was evaluated as good. The results of the respective experiments are shown in TABLE 3.

TABLE 3

| | Composition before Test | | Composition after Test | | | Oil | Microscopic |
|---|---|---|---|---|---|---|---|
| | 1223Z mol % | t-DCE mol % | 1223Z mol % | t-DCE mol % | Kind of Oil | Removing Rate (%) | Observation Result |
| Example 3-1 | 20.001 | 79.999 | 20.043 | 79.957 | cutting oil | 100 | good |
| Example 3-2 | | | 20.037 | 79.963 | turbine oil | 100 | good |
| Example 3-3 | | | 20.088 | 79.912 | lubricating oil | 100 | good |
| Example 3-4 | | | 20.03 | 79.97 | silicone oil A | 100 | good |
| Example 3-5 | | | 20.041 | 79.959 | silicone oil B | 100 | good | cutting oil: Lub Cut B-35 available from Japan Energy Corporation
turbine oil: available from JX Nippon Oil & Energy Corporation, ISO viscosity grade: 68
lubricating oil: SUNISO 4GS available from Japan Sun Oil Co., Ltd.
silicone oil A: KF54 available from Shin-Etsu Chemical Co., Ltd.
silicon oil B: KF96 available from Shin-Etsu Chemical Co., Ltd.

The invention claimed is:

1. An azeotrope-like composition comprising 0.0001 mol % to 40 mol % of (Z)-1,2-dichloro-3,3,3-trifluoropropene and 99.9999 mol % to 60 mol % of (E)-1,2-dichloro-ethylene.

2. The azeotrope-like composition according to claim 1, which comprises 10 mol % to 40 mol % of the (Z)-1,2-dichloro-3,3,3-trifluoropropene and 90 mol % to 60 mol % of the (E)-1,2-dichloro-ethylene.

3. An azeotropic composition consisting essentially of 20 mol % of (Z)-1,2-dichloro-3,3,3-trifluoropropene and 80 mol % of (E)-1,2-dichloro-ethylene.

4. A liquid composition, comprising the azeotrope-like composition according to claim 1 and at least one additional component.

5. The liquid composition according to claim 4, wherein the at least one additional component is contained in an amount of 10 ppm to 30 mass % relative to a total amount of the azeotrope-like composition.

6. A liquid composition, comprising the azeotropic composition according to claim 3 and at least one additional component.

7. The liquid composition according to claim 6, wherein the at least one additional component is contained in an amount of 10 ppm to 30 mass % relative to a total amount of the azeotropic composition.

8. A solvent for cleaning, comprising the azeotrope-like composition according to claim 1.

9. A solvent for cleaning, comprising the azeotropic composition according to claim 3.

10. A method for cleaning a cleaning target object, comprising bringing a cleaning agent into contact with the cleaning target object, wherein the cleaning agent comprises the azeotrope-like composition according to claim 1.

11. A method for cleaning a cleaning target object, comprising bringing a cleaning agent into contact with the cleaning target object, wherein the cleaning agent comprises the azeotropic composition according to claim 3.

12. A method for cleaning a target object, comprising brining a cleaning agent into contact with the cleaning target object, wherein the cleaning agent comprises an azeotrope-like composition comprising (Z)-1,2-dichloro-3,3,3-trifluoropropene and (E)-1,2-dichloro-ethylene.

* * * * *